(12) United States Patent
Tian et al.

(10) Patent No.: US 9,463,220 B2
(45) Date of Patent: Oct. 11, 2016

(54) METHOD FOR INDUCING TWIN CALVING

(71) Applicant: China Agricultural University, Beijing (CN)

(72) Inventors: Jianhui Tian, Beijing (CN); Weibin Zeng, Beijing (CN); Lei An, Beijing (CN); Shumin Wang, Beijing (CN); Zhonghong Wu, Beijing (CN)

(73) Assignee: China Agricultural University, Beijing (CN)

( * ) Notice: Subject to any disclaimer, the term of this patent is extended or adjusted under 35 U.S.C. 154(b) by 0 days.

(21) Appl. No.: 14/285,541

(22) Filed: May 22, 2014

(65) Prior Publication Data
US 2014/0349934 A1    Nov. 27, 2014

(30) Foreign Application Priority Data

May 23, 2013   (CN) .......................... 2013 1 0195475

(51) Int. Cl.
    *A61K 38/24*    (2006.01)
    *A61K 31/57*    (2006.01)
    *A61K 31/566*   (2006.01)
    *A61K 31/557*   (2006.01)

(52) U.S. Cl.
    CPC ............. *A61K 38/24* (2013.01); *A61K 31/557* (2013.01); *A61K 31/566* (2013.01); *A61K 31/57* (2013.01)

(58) Field of Classification Search
None
See application file for complete search history.

(56) References Cited

U.S. PATENT DOCUMENTS

2004/0266697 A1* 12/2004 McSweeney et al. .......... 514/16

OTHER PUBLICATIONS

Bó et al., Theriogenology, 2006; 65: 89-101.*
Son et al., Journal of Reproduction and Development, 2007; 53: 1299-1303.*
Saxena and Rathnam, JBC, 1967; 3769-3775.*
Martinez et al., Therionology, 2000; 54: 757-769.*
Baruselli et al., Theriogenology, 2006; 65: 77-88.*
Pradhan et al., Reproductive Medicine and Biology 2008; 7: 55-62.*
Fike et al., J. Anim. Sci. 1997. 75: 2009-2015.*
Gomez de Sá Filho, Veterinary Medicine International; vol. 2011, Article ID 923053, 10 pages total: doi:10.4061/2011/923053.*
Wiltbank et al., "Managing the dominant follicle in high-producing dairy cows," Editors: Lucy, MC; Pate, JL; Smith, MF; Spencer, TE in Reproduction in Domestic Ruminants VII, 2010: 231-245; Publisher: Nottingham University Press, Sutton Bonnington Campus, Loughborough LE12 5RD, UK. Series: Society of Reproduction and Fertility.*
Yaakub et al., Animal Reproduction Science, 1998; 52: 191-204.*

* cited by examiner

*Primary Examiner* — Christina Borgeest
(74) *Attorney, Agent, or Firm* — Seed IP Law Group PLLC

(57) ABSTRACT

The present invention provides a method for inducing twin calving. The method according to the present invention comprises firstly treatment to inducing atresia of the antral follicles on ovary so as to initiate the development of new follicular wave, inducing the development of codominant follicles and further achieving double ovulations by exactly controlling the dosage and time points of hormone injections, and performing artificial insemination to induce the cow to deliver twin calves. The method according to the present invention has relative independent on the technical skills, and a person skilled in the art or a common worker can practice it according to specified operation methods; and during practical application, it does not require special equipment, thus saving cost, as well as improving the social benefit and economic benefit of cow breeding.

10 Claims, 1 Drawing Sheet

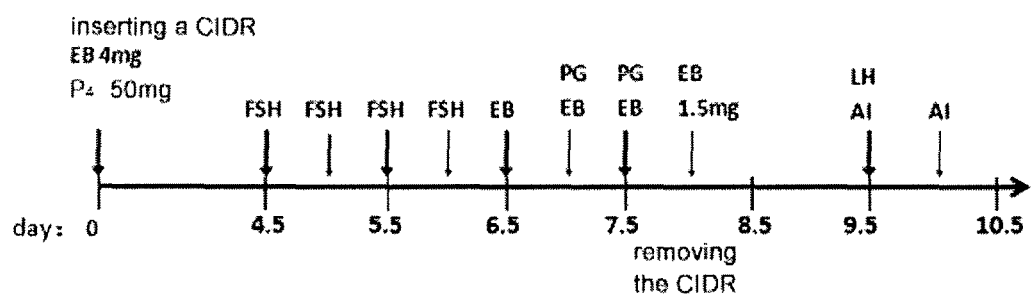

METHOD FOR INDUCING TWIN CALVING

TECHNICAL FIELD

The invention relates to the field of livestock reproduction, particularly to a method for inducing twin calving.

BACKGROUND ART

Cattle are monovular and produce only one calf per year in the natural state. For improving the reproductive efficiency of cow, effects have been conducted to control the number of dominant follicles in the ovary by using various methods, and induce to form codominant follicles and then ovulate two follicles, thereby achieving the purpose of producing two calves.

Currently, several methods are frequently used to induce a cow to produce two calves, which were showed as follow: (1) Hormone induction method: using hormones such as PMSG or FSH (TAN Niannian, 2000; WANG Zhengchen, 2004) to induce a cow to produce two calves through early-stage small-dosage treatment, however, the half-life of PMSG is long, and thus the development of follicles would be disturbed consistently, therefore the stability and feasibility of this method is poor; further, with respect to the method by treatment with FSH alone, the number of codominant follicles cannot be easily controlled, therefore it is not feasible and convenient for practical application. (2) Mechanical aspiration method: aspirating all of the follicles ≥4 mm 4-6 days after ovulation by virtue of a B ultrasound machine (Acosta et al., 2005; Palhao et al., 2009) so as to make the concentration of FSH decrease to the lowest level on the day of aspiration (Kulick et al., 2001), thereafter, the elevation of FSH and the emergence of new follicular wave are just synchronous, thus increasing the probability of producing codominant follicles. (3) Hormone plus mechanical aspiration method: a study (G. Glick et al., 2013) has used small doses of FSH to induce double ovulations of a cow. Although 2-3 ovulations can be achieved at the rate of 90%, the procedure thereof comprises using special estrus synchronization treatment 13 days before the experiment, and aspirating more than 3 large follicles via vaginal wall by using a B ultrasound machine on day 7 of the experiment, so as to achieve the purpose of 2-3 ovulations. Therefore, it is difficult to popularize in the production due to high technical operation and expensive instruments required by follicle aspiration. (4) Inhibitor immunization: some studies used inhibin (gene) immunization (YANG Liguo, 2002; WANG Shuilian, 2009) to adjust the endogenous secretion of FSH, and achieved some effects, but the extraction and the purification of inhibin and the preparation of gene vaccine are complex, and commercial drugs are not commercialized yet, thus it is not popularized in the practice.

All above these methods have defects such as poor stabilization or difficult operational technology, and are difficult to be generalized and applied practically. Hence, there is a need to develop a simple and practical method for inducing twin calving in the field application.

SUMMARY

The object of the present invention is to provide a method for inducing a cow to deliver twin calves, so as to overcome the disadvantages of the present method, which is largely dependent on the technical skill and need a high cost of devices.

For achieving the above object, a method for inducing twin calving according to the present invention comprises following steps:

step 1) on day 0 of the treatment, inserting an intravaginal progesterone releasing device in a cow and injecting progestin and estrogen to cause atresia of antral follicles and initiate a new follicular wave;

step 2) on day 4.5-6, injecting follicle-stimulating hormone (FSH) for 4 times at 10-14 h intervals with sequential dosages of 5.5-6.5 U/cow, 5.5-6.5 U/cow, 4.5-5.5 U/cow and 4.5-5.5 U/cow, leading to the development of codominant follicles in the new follicular wave;

step 3) on day 6.5-7.5, injecting estrogen to inhibit the secretion of FSH through negative feedback, so as to inhibit further development of small follicles that have not been dominant;

step 4) on day 8, removing the intravaginal progesterone releasing device and injecting estrogen to induce the large follicles to ovulate;

step 5) on days 9.5-10, performing artificial insemination (AI).

In the step 1), the injection dosages of the progestin and the estrogen are 45-55 mg/cow and 3.5-4.5 mg/cow respectively, preferably 50 mg/cow and 4 mg/cow;

In the step 2), preferably, on days 4.5-6, FSH is injected 4 times at 12 h intervals with sequential dosages of 6 U/cow, 6 U/cow, 5 U/cow and 5 U/cow;

In the step 3), on days 6.5-7.5, the estrogen is injected 3 times at 10-14 h intervals with each dosage of 0.15-0.25 mg/cow, and prostaglandin (PG) is additionally injected with each dosage of 20-30 mg/cow in the last 2 times respectively. Preferably, the estrogen is injected in 3 times at 12 h intervals with each dosage of 0.2 mg/cow, and PG is additionally injected with each dosage of 25 mg/cow with the last 2 times of the estrogen injections, respectively;

In the step 4), on day 8, the intravaginal progesterone releasing device is removed, and the estrogen is injected at dosage of 1-2 mg/cow, preferably 1.5 mg/cow;

In the step 5), preferably, on days 9.5-10, AI is performed twice, and 2 mg of luteinizing hormone (LH) is injected at the first AI.

The estrogen comprises, but not limited to, estradiol benzoate (EB) or estradiol valerate (EV) injection, preferably EB.

The progestin includes, but not limited to, progesterone ($P_4$) or medroxyprogesteroneacetate (MPA), preferably $P_4$.

A preferable method in Examples of the present invention comprises: on day 0, inserting an intravaginal progesterone releasing device (CIDR), and injecting 4 mg of EB and 50 mg of $P_4$; on days 4.5-6, injecting FSH 4 times at 12 h intervals with dosages of 6 U/cow, 6 U/cow, 5 U/cow and 5 U/cow; on days 6.5-7.5, injecting EB in 3 times at 12 h intervals with a dosage of 0.2 mg/cow·time, wherein PG (lutalyse) is additionally injected with a dosage of 25 mg/cow·time with the last 2 times of EB injections, respectively; on day 8, removing the CIDR, and injecting 1.5 mg of EB; and on day 9.5 and day 10, performing AI twice, and injecting 2 mg of LH in the first AI.

The invention, based on the dynamics and functional characteristics of involved hormones during follicle genesis under cow physiological status, combines several hormones in early-stage treatment to reset new follicular wave, and apply appropriate amount of FSH to the cow before follicle deviation by accurately controlling the treatment time of relevant hormones, so as to induce codominant follicles; small-dosage estrogen is applied and inhibits the secretion of cow endogenous FSH through negative-feedback, so that the development of non-dominant follicles was inhibited, and the codominant follicles whose development has been initiated continues to develop to ovulation stage for not completely depending on FSH during later stage of recruitment. Compared with the conventional methods by using FSH or PMSG alone, the present method can control the development of a small number of follicles (2-3) to deviation stage through deviated small-dosage estrogen treatment, and further achieve the purpose of producing two calves.

In the step 1) of the present invention, a CIDR is inserted into a cow, and progestin and estrogen are injected. It is expected that after 12 h, the concentrations of FSH and LH in cow body will decrease to the lowest level, so that the development of antral follicles in ovary are inhibited, atresia occurs about 36 h after inserting the CIDR, and a new follicular wave starts 4 days later.

In the step 2) of the present invention, small doses of FSH injected before follicle deviation so as to induce the development of codominiant follicles; and in the step 3), after startup of the codominiant follicles, estrogen is injected to inhibit the secretion of FSH by negative feedback, so that the development of non-dominant follicles is inhibited, so as to ensure that the number of dominant follicles is not increased.

The steps 4) and 5) of the present invention realizes the ovulation of dominant follicles and achieves twin calving production through artificial insemination.

The method according to the present invention has a lower dependency on technical skill, and may be practiced by a person skilled in this field or a common worker according to specified operation methods; in addition, this method does not require special equipment, thus ensuring operation feasibility under large-scale production condition.

For a long time, the low reproductive rate of cow results in high feeding cost and low economic benefit. However, the method based on the present invention can induce a cow to double ovulate and deliver twin calves. On one hand, it can rapidly propagate productive group, increase milk yield or meat yield and further improve breeding benefit; on the other hand, it can reduce the feed amount of cow by improving the utilization efficiency of cow, and therefore effectively control the cost of feeding and management and thereby alleviate the environmental pollution caused by largely breeding of cow.

BRIEF DESCRIPTION OF THE DRAWING

FIG. 1 is the flow diagram of the method according to the present invention.

EXAMPLES

Following examples are used for further illustrating the present invention, but should not be understood to limit the present invention. All modifications or equivalent replacements to the present invention without departing from the spirit and the substance of the present invention are covered in the scopes of the appended Claims.

Example 1

According to the flow diagram shown in FIG. 1, 15-18-month-aged cows (30 of Simmental beef cows and 30 of Holstein dairy cows) are treated. On day 0 of the treatment, a CIDR (US Pfizer, USA) is inserted into each of the cows, and 4 mg of EB (Ningbo SANSHENG, China) and 50 mg of $P_4$ (Ningbo SANSHENG, China) are injected; on days 4.5-6, FSH (SIOUX, USA) is injected 4 times at 12 h intervals with dosages of 6 U/cow, 6 U/cow, 5 U/cow and 5 U/cow; on days 6.5-7.5, EB (Ningbo SANSHENG, China) is injected 3 times at 12 h intervals with dosage of 0.2 mg/cow·time, wherein PG (lutalyse, US Pfizer, USA) is additionally injected with the last 2 times of EB injections respectively with dosage of 25 mg/cow·time; on day 8, the CIDR is removed, and 1.5 mg of EB is injected; and on day 9.5 and day 10, AI is performed twice, and 2 mg of LH (Ningbo SANSHENG, China) is injected in the first AI.

The results show that: after the artificial insemination according to the present invention, first-cycle conception rate is 80%, calving rate (calving cow/inseminated cow) is 78%, and two-calf rate (cows delivering twin-calves cow/calving cows) is 62.5%, while after conventional artificial insemination, first-cycle conception rate is 60%, and calving rate is 55%. Thus, the present invention can significantly improve the reproductive efficiency of cow, and achieve a satisfying effect both in beef and dairy cow.

What is claimed is:

1. A method for inducing a cow to produce two calves, comprising:
    step 1) on day 0 of the treatment, inserting an intravaginal progesterone releasing device into said cow and injecting progestin and estrogen so as to cause follicular atresia and initiate the development of a new follicular wave;
    step 2) on days 4.5-6, injecting follicle-stimulating hormone (FSH) 4 times at 10-14 h intervals with sequential dosages of 5.5-6.5 U/cow, 5.5-6.5 U/cow, 4.5-5.5 U/cow and 4.5-5.5 U/cow, leading to the development of codominant follicle in the new follicular wave;
    step 3) on days 6.5-7.5, injecting estrogen to inhibit the secretion of FSH through negative feedback, so as to inhibit non-dominant follicles from further developing;
    step 4) on day 8, removing the intravaginal progesterone releasing device and injecting estrogen to induce the dominant follicles to ovulate; and
    step 5) on days 9.5-10, performing artificial insemination (AI).

2. The method according to claim 1, wherein the dosages of progestin and estrogen in step 1) are 45-55 mg/cow and 3.5-4.5 mg/cow respectively.

3. The method according to claim 2, wherein the dosages of progestin and estrogen in step 1) are 50 mg/cow and 4 mg/cow respectively.

4. The method according to claim 1, wherein on day 4.5-6, FSH is injected 4 times at 12 h intervals at sequential dosages of 6 U/cow, 6 U/cow, 5 U/cow and 5 U/cow, respectively.

5. The method according to claim 1, wherein on day 6.5-7.5, the estrogen is injected 3 times at 10-14 h intervals at a dosage of 0.15-0.25 mg/cow, and further, prostaglandin (PG) is injected at a dosage of 20-30 mg/cow with the last 2 estrogen injections.

6. The method according to claim 5, wherein on day 6.5-7.5, the estrogen is injected 3 times at 12 h intervals at a dosage of 0.2 mg/cow, and further, PG is injected at a dosage of 25 mg/cow with the last 2 estrogen injections.

7. The method according to claim 1, on day 8, the intravaginal progesterone releasing device is removed, and the estrogen is injected at a dosage of 1-2 mg/cow.

8. The method according to claim 1, wherein on day 9.5 and day 10, artificial insemination is performed twice, and further, luteinizing hormone (LH) is injected at a dosage of 2 mg/cow in the first artificial insemination.

9. The method according to claim 1, wherein the estrogen is estradiol benzoate (EB).

10. The method according to claim 1, wherein the progestin is progesterone ($P_4$).

\* \* \* \* \*